(12) United States Patent
Hildbrand et al.

(10) Patent No.: US 6,350,898 B1
(45) Date of Patent: Feb. 26, 2002

(54) PROCESS FOR PREPARING MALONIC ESTERS

(75) Inventors: Stefan Hildbrand, Visp; Paul Hanselmann, Brig-Glis, both of (CH)

(73) Assignee: Lonza AG (CH)

( * ) Notice: Subject to any disclaimer, the term of this patent is extended or adjusted under 35 U.S.C. 154(b) by 0 days.

(21) Appl. No.: 09/480,165

(22) Filed: Jan. 10, 2000

(30) Foreign Application Priority Data

Jan. 11, 1999 (EP) .............................................. 99100411

(51) Int. Cl.⁷ ......................... C07C 69/34; C07C 69/52; C07C 67/00; C07C 55/00
(52) U.S. Cl. ...................... 560/193; 560/201; 560/203; 560/204; 562/590
(58) Field of Search ................................ 560/193, 201, 560/204, 203; 562/590

(56) References Cited

U.S. PATENT DOCUMENTS 3,931,290 A * 1/1976 Bourgau
5,777,151 A * 7/1998 Crochemore

FOREIGN PATENT DOCUMENTS

| DE | 2359963 | | 6/1975 |
|---|---|---|---|
| DE | 2524389 | | 12/1976 |
| DE | 4107986 | | 9/1992 |
| EP | 0 534 817 A1 | | 3/1993 |
| GB | 916772 | * | 1/1963 |
| GB | 966266 | * | 8/1964 |

OTHER PUBLICATIONS

Jaime de la Zerda et al., "Selective Monoetherification and Monoesterification of Diols and Diacids Under Phase-Transfer Conditions", *Tetrahedron*, vol. 45, No. 5, 1989, pp. 1533 to 1536.

* cited by examiner

*Primary Examiner*—Paul J. Killos
*Assistant Examiner*—Mahreen Chaudhry
(74) *Attorney, Agent, or Firm*—Fisher Christen & Sabol

(57) ABSTRACT

Malonic esters of the general formula

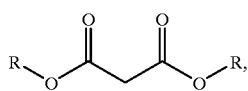

I where R is $C_{1-10}$-alkyl, $C_{3-10}$-alkenyl or aryl-$C_{1-4}$-alkyl, are prepared by reacting an alkali metal salt of malonic acid with a halide of the general formula R—X (II), where R is as defined above and X is chlorine, bromine or iodine, in the presence of water and a phase-transfer catalyst.

2 Claims, No Drawings

PROCESS FOR PREPARING MALONIC ESTERS

BACKGROUND OF THE INVENTION

1. Field of the Invention

The invention relates to a process for preparing malonic esters of the general formula

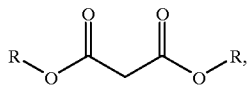

where R is $C_{1-10}$-alkyl, $C_{3-10}$-alkenyl or aryl-$C_{1-4}$-alkyl.

2. Background Art

The two customary methods of preparing malonic esters start from derivatives of chloroacetic acid. In one method, an ester of chloroacetic acid is reacted with carbon monoxide an alcohol in the presence of a catalyst based on cobalt carbonyl (German Published Patent Application Nos. 2359963 and 2524389) while in the other method a salt of chloroacetic acid is reacted with cyanide to form cyanoacetate in a first step and this intermediate is then reacted with an alcohol in a second step to convert it into the malonic ester. The latter method in particular is associated with safety and ecological problems owing to the toxicity of hydrocyanic acid and cyanides and the large amounts of waste. The obvious method of preparing esters by direct esterification of the acid with the appropriate alcohol plays no role in this case; conversely, malonic acid is prepared by hydrolysis of malonic esters (or cyanoacetic acid).

BROAD DESCRIPTION OF THE INVENTION

It is an object of the present invention to provide an alternative route to malonic esters.

This object is achieved according to the invention by the process of the invention.

It has been found that alkali metal salts of malonic acid can be reacted with halides of the general formula R—X (II), where R is $C_{1-10}$-alkyl, $C_{3-10}$-alkenyl or aryl-$C_{1-4}$-alkyl and X is chlorine, bromine or iodine, in the presence of water to give the corresponding malonic esters of the general formula:

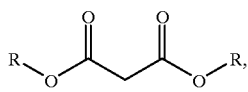

where R is as defined above, if a phase-transfer catalyst is present.

Here and in the following, $C_{1-10}$-alkyl can be any linear or branched, primary, secondary or tertiary alkyl group having 1 to 10 carbon atoms, for example, methyl, ethyl, propyl, isopropyl, butyl, isobutyl, sec-butyl, tert-butyl, pentyl, isopentyl, neopentyl, hexyl, heptyl, octyl, nonyl, decyl, etc.

$C_{3-10}$-alkenyl is a linear or branched alkenyl group having 3 to 10 carbon atoms, in particular one whose double bond is separated from the free valence by at least one saturated carbon atom, for example, allyl, methallyl, 2-butenyl (crotyl), 3-butenyl, 2-pentenyl, etc.

Aryl-$C_{1-4}$-alkyl is, in particular, a phenyl-substituted $C_{1-4}$alkyl group such as benzyl, phenethyl or 3-phenylpropyl, where the phenyl group may also bear one or more identical or different substituents such as $C_{1-4}$-alkyl, $C_{1-4}$-alkoxy or halogen.

Here and in the following, phase-transfer catalysts are the compounds customarily used for this purpose, in particular quaternary ammonium or phosphonium salts.

As alkali metal salt of malonic acid, preference is given to using disodium malonate.

As halide R—X (II), preference is given to using a chloride or bromide.

The alkali metal salt of malonic acid is preferably used in the form of an aqueous solution. Particular preference is given to the solutions obtained by catalytic oxidation of 1,3-propanediol in the presence of aqueous alkali metal hydroxide. The preparation of such solutions is described, for example, in German Published Patent Application No. 4107986.

As phase-transfer catalyst, preference is given to using a quaternary ammonium salt. Particular preference is given to tetra-n-$C_{4-10}$-alkylammonium, benzyltri-n-$C_{1-8}$-alkylammonium and methyltri-n-$C_{4-10}$-alkylammonium halides, where halide is preferably chloride or bromide. Examples which may be mentioned here are tetrabutylammonium and tetrahexylammonium bromides and benzyltributylammonium chloride.

The process of the invention is advantageously carried out at temperatures of 80° to 150° C., when using low-boiling halides (II) conveniently under superatmospheric pressure.

Apart from water, it is advantageous to use an inert solvent which is not miscible with water. Examples of suitable solvents of this type are relatively unreactive aliphatic or aromatic chlorinated hydrocarbons such as chlorobenzene or ethers such as tert-butyl methyl ether.

DETAILED DESCRIPTION OF THE INVENTION

The following examples illustrate the manner in which the process of the invention may be carried out, without implying a restriction.

EXAMPLE 1

Dimethyl Malonate

In an autoclave, 10 g (about 0.2 mol) of methyl chloride were passed into a solution of 2.96 g (20 mmol) of disodium malonate and 0.64 g (2 mmol) of tetrabutylammonium bromide in 5 ml of water while cooling in ice. The mixture was heated to 100° C. over a period of 45 minutes, with the pressure in the autoclave rising from 4 bar to 14 bar. After a reaction time of 3 hours at 100° C., the mixture was cooled to room temperature and depressurized. The aqueous phase was brought from pH 4.6 to pH 5.7 using 1 M sodium hydroxide solution and extracted with tert-butyl methyl ether (2×10 ml). The combined organic phases were dried over sodium sulfate and analyzed by gas chromatography (internal standard: dimethyl succinate). The product yield was 48 percent.

A yield of 46 percent was obtained in tert-butyl methyl ether/water (v:v=8:5) as reaction medium under otherwise identical conditions.

EXAMPLE 2

Diethyl Malonate

In an autoclave, 10.9 g (0.1 mol) of ethyl bromide were added to a solution of 2.96 g (20 mmol) of disodium malonate and 0.64 g (2 mmol) of tetrabutylammonium bromide in 5 ml of water and 10 ml of tert-butyl methyl ether. The mixture was heated to 100° C. over a period of 30 minutes, with the pressure in the autoclave rising to 3.5 bar. After a reaction time of 3½ hours at 100° C., the mixture was cooled to room temperature and depressurized. The aqueous phase was brought from pH 4.2 to pH 5.5 using 1 M sodium hydroxide solution and extracted with tert-butyl methyl ether (2×5 ml). The combined organic phases were dried over sodium sulfate and analyzed by gas chromatography (internal standard: dimethyl succinate). The product yield was 45 percent.

EXAMPLE 3

Dibenzyl Malonate

In an autoclave, 17.1 g (0.1 mol) of benzyl bromide were added to a solution of 2.96 g (20 mmol) of disodium malonate and 0.64 g (2 mmol) of tetrabutylammonium bromide in 5 ml of water and 10 ml of tert-butyl methyl ether. The mixture was heated to 100° C. over a period of 30 minutes, with the pressure in the autoclave rising to 2.5 bar. After a reaction time of 3 ½ hours at 100° C., the mixture was cooled to room temperature and depressurized. The aqueous phase was brought from pH 1.8 to pH 5.8 using 1 M sodium hydroxide solution and extracted with tert-butyl methyl ether (2×5 ml). The combined organic phases were dried over sodium sulfate, the solvent was distilled off on a rotary evaporator and the residue was freed of solvent residues under reduced pressure (1 mbar). The product yield was 2.43 g (43 percent). Other data concerning the product was:

$^1$H NMR (CDCl$_3$, 400 MHz): δ=7.25–7.40 (m, 10H); 5.16 (s, 4H); 3.47 (s, 2H).

When using benzyl chloride instead of benzyl bromide, a yield of 34 percent was obtained under identical reaction conditions.

EXAMPLE 4

Diallyl Malonate

In an autoclave, 7.65 g (0.1 mol) of allyl chloride were added to a solution of 2.96 g (20 mmol) of disodium malonate and 0.64 g (2 mmol) of tetrabutylammonium bromide in 5 ml of water and 10 ml of chlorobenzene. The mixture was heated to 100° C. over a period of 30 minutes, with the pressure in the autoclave rising to 2.5 bar. After a reaction time of 3½ hours at 100° C., the mixture was cooled to room temperature and depressurized. The aqueous phase was extracted with tert-butyl methyl ether (2×5 ml). The combined organic phases were dried over sodium sulfate and analyzed by gas chromatography (internal standard: dimethyl succinate). The product yield was 16 percent.

EXAMPLES 5 to 12

Dimethyl Malonate

General Procedure:

In an autoclave, 10 g (0.2 mol) of methyl chloride were passed into a solution of 2.96 g (20 mmol) of disodium malonate and 0.1 equivalents (2 mmol) of the phase-transfer catalyst in 5 ml of water and 10 ml of chlorobenzene while cooling in ice. The mixture was heated to the desired temperature over a period of 30 minutes. After a reaction time of 3 hours at the appropriate temperature, the mixture was cooled to room temperature and depressurized. The aqueous phase was brought to pH 5.5 to 6.5 using 1 M sodium hydroxide solution and extracted with tert-butyl methyl ether (2×10 ml). The combined organic phases were dried over sodium sulfate and analyzed by gas chromatography (internal standard: dimethyl succinate). The reaction conditions and the yields achieved are summarized in Table 1 below:

| Example No. | Catalyst[1] | Temperature (° C.) | Reaction time [h] | Yield[2] [%] |
|---|---|---|---|---|
| 5 | TBAB | 100 | 4 | 55 |
| 6 | TBAB | 100 | 6 | 56 |
| 7 | TBAB | 125 | 5 | 64 |
| 8 | TBAB | 150 | 4 | 6 |
| 9 | TBAB | 100 | 4 | 58 |
| 10 | BTBAC1 | 100 | 4 | 39 |
| 11 | THAB | 125 | 4 | 67 |
| 12[3] | THAB | 100 | 4 | 21 |

Notes:
[1]TBAB = tetrabutylammonium bromide, THAB = tetrahexylammonium bromide, and BTBAC1 = benzyltributylammonium chloride
[2]GC, internal standard: dimethyl succinate
[3]With the addition of 10 mol percent of KBr

What is claimed is:

1. A process for preparing a malonic ester of the formula:

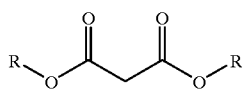

I wherein R is C$_{1-10}$-alkyl, C$_{3-10}$-alkenyl or aryl-C$_{1-4}$-alkyl, comprising reacting an alkali metal salt of malonic acid with a halide of formula R—X(II), wherein R is as defined above and X is chlorine, bromine, or iodine, in the presence of water, an inert solvent which is not miscible with water is present, and a phase-transfer catalyst.

2. The process according to claim 1, wherein the inert solvent is a relatively unreactive aliphatic or aromatic chlorinated hydrocarbon.

* * * * *